United States Patent [19]

Maruyama et al.

[11] Patent Number: 5,837,291
[45] Date of Patent: Nov. 17, 1998

[54] ENTERIC PREPARATION COATED WITH A NON-SOLVENT ENTERIC COATING AGENT USING A LIQUID PLASTICIZER

[75] Inventors: Naosuke Maruyama; Hiroyasu Kokubo, both of Kubiki-Mura, Japan

[73] Assignee: Shin-Etsu Chemical Co., Ltd., Tokyo, Japan

[21] Appl. No.: 657,691

[22] Filed: May 31, 1996

[30] Foreign Application Priority Data

Jun. 2, 1995 [JP] Japan ..................... 7-159766

[51] Int. Cl.$^6$ .............. A61K 9/14; A61K 9/28; A61K 9/54
[52] U.S. Cl. .............. 424/489; 424/458; 424/459; 424/461; 424/462; 424/474; 424/475; 424/480; 424/482; 424/490; 424/494; 424/497
[58] Field of Search ................ 424/475, 480, 424/458, 459, 461, 462, 474, 482, 489, 490, 494, 497

[56] References Cited

U.S. PATENT DOCUMENTS

| 2,373,763 | 4/1945 | Kuever et al. | 424/475 |
| 4,462,839 | 7/1984 | McGinley et al. | 424/480 |
| 5,275,824 | 1/1994 | Carli et al. | 424/490 |
| 5,430,021 | 7/1995 | Rudnic et al. | 424/490 |

*Primary Examiner*—Thurman K. Page
*Assistant Examiner*—James M. Spear
*Attorney, Agent, or Firm*—Townsend&Banta

[57] ABSTRACT

An enteric preparation prepared by coating a solid dosage form with a fine powder enteric coating agent while spraying a liquid plasticizer.

4 Claims, No Drawings

ENTERIC PREPARATION COATED WITH A NON-SOLVENT ENTERIC COATING AGENT USING A LIQUID PLASTICIZER

RELATED APPLICATIONS

This application claims the priority of Japanese Patent application No.7-159766 filed on June 2, which is incorporated herein by reference.

BACKGROUND OF THE INVENTION

1. Field of the Invention

This invention relates to an enteric preparation, and more particularly to an enteric preparation prepared by coating a solid dosage form with a non-solvent enteric coating agent using a liquid plasticizer.

2. The prior Art

An enteric coating is widely used for a variety of purposes including protection of acid sensitive drugs from stomach acid or protection of stomach mucous membranes from drugs which cause irritation and or damage to the stomach wall.

For the enteric coating agent, the cellulose types including cellulose acetate phthalate (CAP), cellulose acetate trimellitate (CAT), hydroxypropylmethyl cellulose phthalate (HPMCP), hydroxypropylmethyl cellulose acetate succinate (HPMCAS) and carboxymethylethyl cellulose (CMEC), the vinyl types including polyvinyl alcohol acetate phthalate (PVAP) and the acrylic types including copolymers of methacrylic acid and ethyl acetate are used.

These coating agents can be used for coating by dissolving the polymer in an organic solvent or as an aqueous latex or an aqueous suspension. Since these methods use an organic solvent or water as the solvent, it takes a long time to spray these coating solution and drying of the solvent takes some time as well. Some drugs are sensitive to contact with water or organic solvents and therefore development of an enteric coating method which does not use solvent has been desired.

Waxes, being hydrophobic and insoluble in water, are generally used to control elution of controlled release preparations. Proposed examples of a combination between these waxes and an enteric coating agent include: Japanese unexamined patent publication Tokkai Sho 56-164114 in which prior art enteric coating is conducted on granules prepared by the wet granulation method using a composition containing a higher fatty acid or its metal salt; Tokkai Sho 62-33128 in which an enteric preparation of interferon is prepared by preparing a micelle with an unsaturated fatty acid and a surfactant in the aqueous system, freeze-drying it, molding it into granules and such, and then giving it an enteric coating; Tokkai Sho 59-20219 in which a composition containing a higher fatty acid is used for undercoating an enteric preparation; and Tokkai Sho 58-46019 in which an enteric coating agent and fat oil are dissolved in a common solvent (ethanol, dichloroethane, etc.) to be used as a controlled release coating of a controlled release preparation of Nifedipine.

However, for all these coating methods, although they used both waxes and an enteric coating, the enteric coating itself is a prior art method using a solvent and it takes a long time for coating and drying.

Proposed examples of coating with waxes include: Tokkai Hei 1-28719 in which a higher fatty acid, higher alcohol, higher fatty acid ester or such which has a melting point of 40° C. or higher is heated above the melting point or dissolved in an organic solvent and a coating pan or a centrifugal flow coating granulation device is used for spray coating, followed by ethyl cellulose or enteric coating; Tokkai Hei 1-287021 in which wax in a powder or pellet form with a melting point of 40°–90° C. is heated and used for coating with a fluidized bed coating appratus; and Tokkai Hei 2-142735 in which coating is done by mechanical stirring using a lipid powder with a melting point of 40° C. or higher. However, these are preparations aimed at masking a bitter taste and a combination with an enteric coating agent is not mentioned.

Tokkai Hei 2-292229 discloses a long-lasting preparation obtained by heating a mixture of a refractory drug, a higher fatty acid which is solid at room temperature and an enteric coating agent and kneading it when the higher fatty acid is melted. However, this is not related to an enteric preparation with acid resistance. Tokkai Sho 62-181214 cites fat/oil, fatty acids and higher alcohols as low melting point substances with a melting point of 30°–100° C. and discloses a method of preparing controlled release particles in which these powder/particles forming low-melting-point substances are used as nuclei to which medicine is adhered by means of fusion for granulation, and the particles thus obtained, while being stirred and tumbled, are heated before talc or such is sprinkled for coating. In this method, the coating film is made tight by additionally using an enteric coating agent finely micronized to have a diameter of 10 micrometers or less during the talc coating process. However, this method is not related to an acid resistant enteric preparation.

BRIEF SUMMARY OF THE INVENTION

Based on the points made above, the inventors conducted earnest research and discovered that an acid resistant enteric preparation can be quickly obtained by means of a non-solvent coating, which does not require drying, and more specifically by putting directly a fine polymeric powder to coating bed while spraying a liquid plasticizer. The present invention was thus completed.

The present invention provides an enteric preparation prepared by coating a solid dosage form with a fine powder enteric coating agent while spraying a liquid plasticizer.

The present invention also provides an enteric preparation wherein said solid dosage form is granules or parvules of the active ingredient.

The present invention also provides an enteric preparation wherein said liquid plasticizer is triethyl citrate.

The present invention also provides an enteric preparation wherein the particle diameter of said fine powder enteric coating agent is 10 micrometers or less.

DETAILED DESCRIPTION

The present invention is described in detail below.

The enteric preparation of the present invention is characterized by coating a solid dosage form with a fine powder enteric coating base agent while spraying a liquid plasticizer.

Selection of the plasticizer used in the present invention is not particularly limited as long as it can fuse the hydrophobic fine powder enteric coating agent. Examples include triethyl citrate, triacetin and dibutyl phthalate. Of these, triethyl citrate is preferable because it has a greater effect of fusing the enteric preparation. These plasticizers can be used independently or in combinations of two or more.

When the enteric coating agent is used in the coating process, hydrophobic waxes including higher alcohols, higher fatty acids and glycerine fatty acid esters can be added to improve the water resistance of the obtained enteric preparation.

Also, it is possible to use water soluble polyhydric alcohols such as polyethylene glycol to obtain a controlled release preparation.

Since the present invention sprinkles a fine powder enteric coating agent for coating, the applicable solid dosage form is preferably granules, parvules or the active ingredient. It is preferable for them to be closer to a spherical form because then the amount of the enteric coating agent required to achieve acid resistance is less.

The enteric coating agent used in the present invention should be a fine powder of 10 micrometers or less. For example, the cellulose types including cellulose acetate phthalate (CAP), cellulose acetate trimellitate (CAT), hydroxypropylmethyl cellulose phthalate (HPMCP), hydroxypropylmethyl cellulose succinate (HPMCAS) and carboxymethylethyl cellulose (CMEC), the vinyl types including polyvinyl alcohol acetate phthalate (PVAP) and the acrylic types including copoylmers of methacrylic acid and ethyl acrylate can be used. If the average particle sized is more than 10 micrometers, then the coating agent may not stick well to the granules, resulting in failed coating.

Of these coating agents, hydroxypropylmethyl cellulose acetate succinate (HPMCAS), which has a low softening temperature and superior film forming properties, is preferable.

It is also possible to use a polymer fine powder, such as ethyl cellulose and acrylic polymer, in addition to the enteric coating agent to obtain a controlled release preparation.

Implementation of the present invention does not require significant drying power because a solvent is not used. It is preferable to have some heating and stirring capability for extension and fusion of the sprinkled fine powder enteric coating agent. Examples of the apparatus include the centrifugal flow coating apparatus, pan coating apparatus and fluidized bed coating apparatus. Of these coating apparatuses, the centrifugal flow coating apparatus with adequate stirring capability is preferable.

Coating using the enteric coating agent comprises, for example, stirring and tumbling granules or parvules of the solid dosage form while a plasticizer which is liquid at room temperature or a heat-melted liquid plasticizer is sprinkled or sprayed on them and simultaneously the enteric coating agent of 10 micrometers or less is sprinkled to coat the solid dosage form. This series of operations can also be conducted by dividing it into several batches with different compositions. It is also possible to additionally sprinkle talc, aerosil ($SiO_2$), magnesium stearate or corn starch in order to prevent the granules from adhering to each other during the coating process.

In the present invention, the weight ratio between the plasticizer and the enteric coating agent and the amount of coating for the solid dosage form are important factors for obtaining acid resistance. Although they vary significantly depending on the water solubility of the medicine used, the composition ratio of medicines in the solid dosage form (granules and such), etc., the ratio (plasticizer:enteric coating agent) is generally within the range of 2:8 to 8:2. If the plasticizer content is higher than this range, then disintegration in pharmacopoeia Japonica No. 2 solution (pH 6.8) does not occur. If it is lower than this range, then fusion of the enteric coating agent becomes insufficient.

The amount of coating is generally within the range of 10–50 wt % when expressed as the ratio of the enteric coating agent and the solid dosage form to be coated.

Since the enteric coating agent is sprinkled for coating in the present invention, the treatment time is very short even when the amount of coating increases.

The enteric coating agent of the present invention thus obtained can be additionally coated with another polymer compound. Pharmaceutically approved medicines, additives (plasticizers, colorings, pigments, anti-adhesion agents (talc), oils/fats, etc.) may be added to these coatings.

Conventional enteric coating is performed by using an organic solvent solution, aqueous latex or water dispersion of an enteric coating agent. Therefore, spraying takes a long time and additional time to dry the solvent is also required and there is a problem in that some medicines are sensitive to exposure to water or organic solvents, or to heating during the drying process.

According to the present invention, an acid resistant enteric preparation can be obtained by non-solvent coating which only takes a short time and does not require a drying process. Since drying of the solvent is not necessary (no heating for drying) and the coating time is short, the manufacturing process can be shortened. Also, the non-solvent coating can be applied to medicines which are unstable when exposed to water and organic solvents. Furthermore, there is an advantage in that surfactants and such, which are generally used as a dispersion agent for the aqueous system enteric coating, are not required.

EXAMPLES

The present invention is described in further details below by referring to examples. The present invention is not limited to these examples. In the examples, parts and % are in the weight percent unit.

[Experiment 1: Preparation of granules containing $VB_2$]

2000 g of nucleus granules (Non-Pareil 101 20-24# from Freund Co., Ltd.) were put into a centrifugal flow coating apparatus (CF coater CF-360 from Freund Co., Ltd.). While an aqueous solution of 5% hydroxypropyl cellulose was sprayed, powder prepared by homogeneously mixing 75 g of $VB_2$ and 1175 g of corn starch was sprinkled to prepare the granules. These granules contained 2% $VB_2$.

[Example 1]

400 g of the granules containing 2% $VB_2$ prepared in Experiment 1 were put into the centrifugal flow coating apparatus (CF coater CF-360 from Freund Co., Ltd.). Coating was conducted at an intake temperature of 60° C., a product temperature of 40° C. and a rotation speed of 200 rpm by adding, at 60 g/min, powder prepared by homogeneously mixing 120 g of hydroxypropylmethyl cellulose acetate succinate (average particle size 5 micrometers: AS-MF from Shin-Etsu Chemical Co., Ltd.) and 240 g of talc, while spraying 60 g of triethyl citrate at a rate of 10 g/min. The yield was 95%. The treatment time was 6 minutes. For these coated granules, the elution ratio after 2 hours in No. 1 solution was measured according to the pharmacopoeia Japonica 12 elution test method. The measured elution ratio was 1.5%, indicating superior acid resistance. The disintegration time of these granules was measured according to the pharmacopoeia Japonica 12 disintegration test method. The measured disintegration time was 10 minutes, indicating enteric dissolution.

[Example 2]

400 g of the granules containing 2% $VB_2$ prepared in Experiment 1 were put into the centrifugal flow coating apparatus (CF coater CF-360 from Freund Co., Ltd.). Coating was conducted at an intake temperature of 60° C., a product temperature of 40° C. and a rotation speed of 200 rpm by adding, at 60 g/min, powder prepared by homogeneously mixing 120 g of hydroxypropylmethyl cellulose acetate succinate (average particle size 5 micrometers: AS-MF from Shin-Etsu Chemical Co., Ltd.) and 240 g of talc, while spraying 120 g of triacetin at a rate of 20 g/min. The yield was 95%. The treatment time was 6 minutes. For these coated granules, the elution ratio after 2 hours in No. 1 solution was measured according to the pharmacopoeia Japonica 12 elution test method. The measured elution ratio was 1.5% indicating superior acid resistance. The disintegration time of these granules was measured according to the pharmacopoeia Japonica 12 disintegration test method. The measured disintegration time was 10 minutes, indicating enteric dissolution.

[Example 3]

400 g of the granules containing 2% $VB_2$ prepared in Experiment 1 were put into the centrifugal flow coating apparatus (CF coater CF-360 from Freund Co., Ltd.). Coating was conducted at an intake temperature of 60° C., a product temperature of 40° C. and a rotation speed of 200 rpm by adding, at 40 g/min, powder prepared by homogeneously mixing 120 g of hydroxypropylmethyl cellulose acetate succinate (average particle size 5 micrometers: AS-MF from Shin-Etsu Chemical Co., Ltd.) and 120 g of talc, while spraying 120 g of an ethanol solution of 50% triethyl citrate at a rate of 20 g/min. The yield was 98%. The treatment time was 6 minutes. For these coated granules, the elution ratio after 2 hours in No. 1 solution was measured according to the pharmacopoeia Japonica 12 elution test method. The measured elution ratio was 1.0%, indicating superior acid resistance. The disintegration time of these granules was measured according to the pharmacopoeia Japonica 12 disintegration test method. The measured disintegration time was 11 minutes, indicating enteric dissolution.

[Comparative Example 1]

Water dispersion system coating was conducted on the $VB_2$ granules prepared in Experiment 1 using the following composition containing hydroxypropylmethyl cellulose acetate succinate (AS-MF from Shin-Etsu Chemical Co., Ltd.).

400 g of the $VB_2$ granules were put into a fluidized bed coating apparatus (Multiplex MP-01 from Powrex Co., Ltd.). Coating was conducted at an intake temperature of 80° C., an exhaust temperature of 35° C. and a spray rate of the coating solution of 25 g/min until the ratio of hydroxypropylmethyl cellulose acetate succinate (AS-MF from Shin-Etsu Chemical Co., Ltd.) coating and the bare granules became the same (30%) as in Example 1. The coating yield was 92% and the coating time was 68 minutes. After this, additional drying was done for 30 minutes. The total time required to prepare the coated granules was 98 minutes.

| [Coating solution ingredients] | |
|---|---|
| Hydroxypropylmethyl cellulose acetate succinate (AS-MF from Shin-Etsu Chemical Co., Ltd.) | 7.00% |
| Triethyl citrate | 1.96 |
| Talc | 2.10 |
| Sodium laurylsulfate | 0.21 |
| Water | 88.73 |
| Total | 100.00 |

What is claimed is:

1. A method of preparing an enteric preparation coated with a non-solvent enteric coating agent without drying, said method comprising applying to a solid dosage form a non-solvent coating composition consisting essentially of a fine powder polymeric enteric coating agent while spraying a liquid plasticizer therefor.

2. The method of preparing an enteric preparation coated with a non-solvent enteric coating agent without drying of claim 1, wherein said solid dosage form is granules or parvules of the active ingredient.

3. The method of preparing an enteric preparation coated with a non-solvent enteric coating agent without drying of claim 1, wherein said liquid plasticizer is triethyl citrate.

4. The method of preparing an enteric preparation coated with a non-solvent enteric coating agent without drying of claim 1, wherein the particle diameter of said fine powder polymeric enteric coating agent is 10 micrometers or less.

* * * * *